US011583352B2

(12) United States Patent
Betsugi et al.

(10) Patent No.: US 11,583,352 B2
(45) Date of Patent: Feb. 21, 2023

(54) ENDOSCOPE ADAPTOR, SURGICAL SYSTEM INCLUDING THE SAME, AND METHOD OF ATTACHING ENDOSCOPE TO ROBOT ARM THROUGH THE SAME (71) Applicant: MEDICAROID CORPORATION, Kobe (JP)

(72) Inventors: Shota Betsugi, Kobe (JP); Yu Usuki, Kobe (JP); Kenji Ago, Kobe (JP)

(73) Assignee: MEDICAROID CORPORATION, Kobe (JP)

( * ) Notice: Subject to any disclaimer, the term of this patent is extended or adjusted under 35 U.S.C. 154(b) by 799 days.

(21) Appl. No.: 16/547,530

(22) Filed: Aug. 21, 2019

(65) Prior Publication Data
US 2020/0069386 A1 Mar. 5, 2020

(30) Foreign Application Priority Data
Aug. 28, 2018 (JP) .............................. JP2018-159329

(51) Int. Cl.
*A61B 1/00* (2006.01)
*A61B 34/37* (2016.01)
(Continued)

(52) U.S. Cl.
CPC .......... *A61B 34/37* (2016.02); *A61B 1/00045* (2013.01); *A61B 1/00128* (2013.01);
(Continued)

(58) Field of Classification Search
CPC . A61B 34/37; A61B 1/00045; A61B 1/00128; A61B 1/00133; A61B 1/00142;
(Continued)

(56) References Cited

U.S. PATENT DOCUMENTS 6,436,107 B1 * 8/2002 Wang ..................... A61B 34/75
606/139
6,699,177 B1 * 3/2004 Wang ..................... A61B 34/77
600/102
(Continued)

FOREIGN PATENT DOCUMENTS

| CN | 102630154 A | 8/2012 |
|----|-------------|--------|
| CN | 107530135 A | 1/2018 |

(Continued)

*Primary Examiner* — Timothy J Neal
*Assistant Examiner* — William B Chou
(74) *Attorney, Agent, or Firm* — Metrolex IP Law Group, PLLC (57) ABSTRACT An endoscope adaptor to be connected to a robot arm of a robotic surgical system through a drape adaptor according to an embodiment may include a base section, a holding section, a driven member, and a transmission mechanism. The base is to be detachably connected to the drape adaptor. The driven member is rotatably provided on the base section and configured to be rotated by a rotation drive section of the robot arm through the drape adaptor. The holding section holds an endoscope rotatably about a rotation axis, the endoscope including an insertion section including an image capturing section provided at a distal end of the insertion section and a body section connected to the insertion section, wherein the rotation axis extends in a direction in which the insertion section extends. The transmission mechanism is configured to transmit rotation of the driven member to the holding section holding the endoscope.

22 Claims, 8 Drawing Sheets (51) Int. Cl.
   *A61B 17/29* (2006.01)
   *A61B 18/14* (2006.01)
   *A61B 18/00* (2006.01)
   *A61B 34/30* (2016.01)

(52) U.S. Cl.
   CPC ...... *A61B 1/00133* (2013.01); *A61B 1/00142* (2013.01); *A61B 1/00149* (2013.01); *A61B 17/2909* (2013.01); *A61B 18/148* (2013.01); *A61B 2018/00589* (2013.01); *A61B 2034/301* (2016.02)

(58) Field of Classification Search
   CPC ............ A61B 1/00149; A61B 17/2909; A61B 18/148; A61B 2034/301; A61B 2018/00589
   See application file for complete search history.

(56) References Cited

U.S. PATENT DOCUMENTS

| | | | |
|---|---|---|---|
| 8,998,799 B2 | 4/2015 | Orban, III et al. | |
| 2002/0045905 A1* | 4/2002 | Gerbi | A61B 17/34 606/108 |
| 2004/0049205 A1 | 3/2004 | Lee et al. | |
| 2006/0253108 A1* | 11/2006 | Yu | A61B 90/50 606/1 |
| 2008/0091066 A1* | 4/2008 | Sholev | A61B 90/50 600/112 |
| 2010/0274078 A1* | 10/2010 | Kim | A61B 34/30 600/102 |
| 2012/0265013 A1* | 10/2012 | Yamakawa | A61B 1/00135 600/114 |
| 2012/0277530 A1* | 11/2012 | Yamakawa | A61B 1/00135 600/114 |
| 2013/0172679 A1* | 7/2013 | Ashida | A61B 1/051 600/114 |
| 2014/0276720 A1 | 9/2014 | Parihar et al. | |
| 2015/0119638 A1* | 4/2015 | Yu | A61B 1/018 600/102 |
| 2017/0065363 A1 | 3/2017 | Schuh et al. | |
| 2017/0325905 A1 | 11/2017 | Jogasaki et al. | |
| 2020/0405434 A1* | 12/2020 | Schuh | A61B 34/30 |

FOREIGN PATENT DOCUMENTS

| | | | | |
|---|---|---|---|---|
| EP | 1139881 A1 | 10/2001 | | |
| EP | 1139881 B1 | 11/2009 | | |
| JP | H06-22901 A | 2/1994 | | |
| JP | H09-66487 A | 3/1997 | | |
| JP | 2004-129956 A | 4/2004 | | |
| JP | 2013-208506 A | 10/2013 | | |
| WO | 00/30551 A1 | 6/2000 | | |
| WO | WO-2017044884 A1 * | 3/2017 | ......... | A61B 1/00149 |
| WO | 2019/139941 A1 | 7/2019 | | |

\* cited by examiner

ND OSCOPE ADAPTOR, SURGICAL
SYSTEM INCLUDING THE SAME, AND
METHOD OF ATTACHING ENDOSCOPE TO
ROBOT ARM THROUGH THE SAME

CROSS REFERENCE TO RELATED
APPLICATIONS

This application claims priority to Japanese Patent Application No. 2018-159329 filed on Aug. 28, 2018, the entire contents of which are incorporated herein by reference.

BACKGROUND

The disclosure relates to an endoscope adaptor, and particularly relates to an endoscope adaptor that holds an endoscope, a surgical system that includes the endoscope adaptor, and a method of attaching the endoscope to a robot arm through the endoscope adaptor.

In a related art, there has been known an endoscope holding apparatus that holds an endoscope (e.g., see Japanese Patent Application Publication No. 2004-129956).

Japanese Patent Application Publication No. 2004-129956 discloses an endoscope holding apparatus that includes a mount section including a permanent magnet that attracts and holds a holder section of an endoscope, and a gear section housed in the mount section and meshing with a gear provided in the holder section of the endoscope. The endoscope holding apparatus of Japanese Patent Application Publication No. 2004-129956 is configured such that, when the holder section of the endoscope is attracted to the permanent magnet of the mount section, the gear section of the mount section meshes with the gear of the endoscope and the endoscope is thus rotated by driving of the gear section.

SUMMARY

The endoscope holding apparatus of Japanese Patent Application Publication No. 2004-129956 is configured such that, when the holder section of the endoscope is attracted to the permanent magnet of the mount section, the gear section of the mount section meshes with the gear of the endoscope, and the endoscope is thus rotated by driving of the gear section. In this case, when a drape for clean operation is put between the mount section and the endoscope, the gear section of the mount section does not mesh with the gear of the endoscope. This leads to an inconvenient situation where the endoscope cannot be rotated. In other words, there is a problem of the difficulty in rotatably holding the endoscope while covering the endoscope holding apparatus with the drape.

An object of an embodiment of the disclosure may be to provide an endoscope adaptor that can rotatably hold an endoscope while covering a robot arm holding the endoscope with a drape, a surgical system that includes the endoscope adaptor, and a method of attaching the endoscope to the robot arm through the endoscope adaptor.

A first aspect of an embodiment may be an endoscope adaptor to be connected to a robot arm of a robotic surgical system through a drape adaptor. The endoscope adaptor may include: a base section that is to be detachably connected to the drape adaptor; a driven member that is rotatably provided on the base section and is configured to be rotated by a rotation drive section of the robot arm through the drape adaptor; a holding section that holds an endoscope rotatably about a rotation axis, the endoscope including an insertion section including an image capturing section provided at a distal end of the insertion section and a body section connected to the insertion section, wherein the rotation axis extends in a direction in which the insertion section extends; and a transmission mechanism configured to transmit rotation of the driven member to the holding section holding the endoscope.

A second aspect of an embodiment may be a robotic surgical system that may include: a robot arm that is covered with a drape and includes a rotation drive section; a drape adaptor that is attached to the robot arm and includes a rotation drive transmission member engaged with the rotation drive section; and an endoscope adaptor that is attached to the drape adaptor and includes a driven member engaged with the rotation drive section, a holding section rotatably holding an endoscope, and a transmission mechanism transmitting rotation of the driven member to the holding section.

A third aspect of an embodiment may be a method of attaching an endoscope to a robot arm through a drape adaptor and an endoscope adaptor. The method may include: attaching the endoscope to a holding section of the endoscope adaptor such that the endoscope is rotatably held by the holding section of the endoscope adaptor; attaching the drape adaptor to the robot arm such that a rotation drive section of the robot arm is engaged with a rotation drive transmission member of the drape adaptor in a state where the robot arm is covered with a drape; and attaching an endoscope adaptor that holds the endoscope to the drape adaptor attached to the robot arm such that a driven member of the endoscope adaptor that is configured to transmit rotation to the holding section through a transmission mechanism is engaged with the rotation drive transmission member of the drape adaptor.

DETAILED DESCRIPTION

Descriptions are provided hereinbelow for one or more embodiments based on the drawings. In the respective drawings referenced herein, the same constituents are designated by the same reference numerals and duplicate explanation concerning the same constituents is omitted. All of the drawings are provided to illustrate the respective examples only.

(Configuration of Robotic Surgical System)

The configuration of a robotic surgical system 100 according to an embodiment is described with reference to FIGS. 1 and 2.

Figure 1:
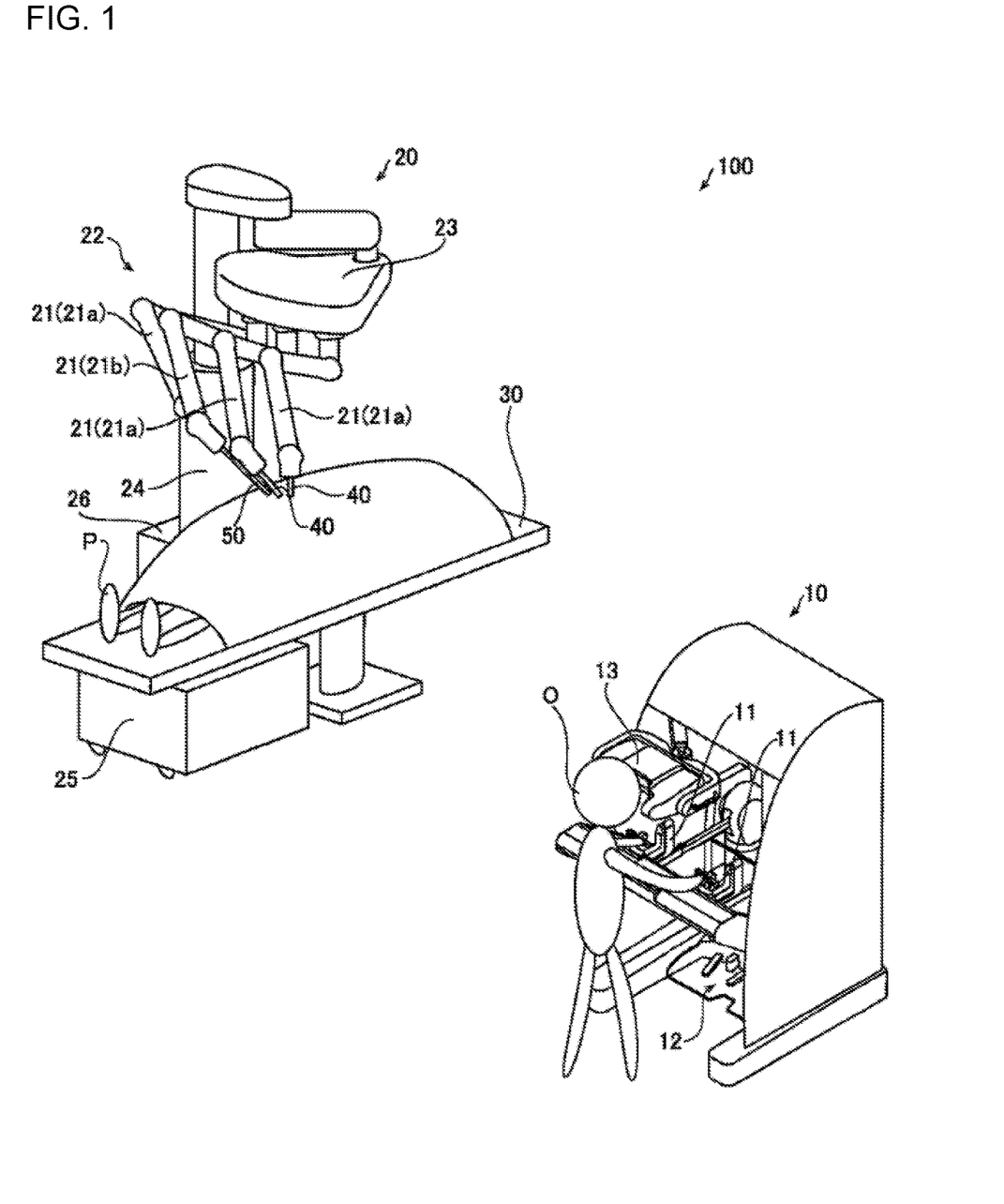
FIG. 1 is a diagram illustrating a view of an overview of a robotic surgical system according to an embodiment.

As illustrated in FIG. 1, the robotic surgical system 100 includes a remote control apparatus 10 and a patient-side apparatus 20. The remote control apparatus 10 is provided to remotely control medical equipment provided for the patient-side apparatus 20. When an operator O, as a surgeon, inputs an action mode instruction to be executed by the patient-side apparatus 20, to the remote control apparatus 10, the remote control apparatus 10 transmits the action mode instruction to the patient-side apparatus 20 through a controller 26. In response to the action mode instruction transmitted from the remote control apparatus 10, the patient-side apparatus 20 operates medical equipment, including surgical instruments 40 and an endoscope 50, attached to robot arms 21. This allows minimally invasive surgery.

The patient-side apparatus 20 constitutes an interface to perform a surgery on a patient P. The patient-side apparatus 20 is positioned beside an operation table 30 on which the patient P is laid. The patient-side apparatus 20 includes robot arms 21. One of the robot arms 21 (21b) holds the endoscope 50 while the other robot arms 21 (21a) hold the surgical instruments 40. The robot arms 21 are commonly supported by a platform 23. Each of the robot arms 21 includes joints. Each joint includes a driver provided with a servo-motor and a position detector such as an encoder. The robot arms 21 are configured so that the medical equipment attached to each robot arm 21 is controlled by a driving signal given through the controller 26 and performs a desired movement.

The platform 23 is supported by a positioner 22 placed on the floor of an operation room. The positioner 22 includes a column 24 and a base 25. The column 24 includes an elevating shaft adjustable in the vertical direction. The base 25 includes wheels and is movable on the floor surface.

The surgical instruments 40 as the medical equipment are detachably attached to the distal ends of the robot arms 21a. Each surgical instrument 40 includes: a housing 43 (see FIG. 3), which is attached to the robot arm 21a; an elongated shaft 42 (see FIG. 3); and an end effector 41 (see FIG. 3), which is provided at the tip or the distal end of the shaft 42. The end effector 41 is grasping forceps, scissors, a hook, a high-frequency knife, a snare wire, a clamp, or a stapler, for example. The end effector 41 is not limited to those and can be various types of treatment tools. In surgeries using the patient-side apparatus 20, the robot arms 21a introduce the surgical instruments 40 into the body of the patient P through a cannula (trocar) placed on the body surface of the patient P. The end effectors 41 of the surgical instruments 40 are then located near the surgery site.

To the distal end of the robot arm 21b, the endoscope 50 as the medical equipment is detachably attached. The endoscope 50 captures an image within the body cavity of the patient P. The captured image is outputted to the remote control apparatus 10. The endoscope 50 is a 3D endoscope capable of capturing a three-dimensional image or a 2D endoscope. In surgeries using the patient-side apparatus 20, the robot arm 21b introduces the endoscope 50 into the body of the patient P through a trocar placed on the body surface of the patient P. The endoscope 50 is then located near the surgery site.

The remote control apparatus 10 constitutes the interface with the operator O. The remote control apparatus 10 is an apparatus that allows the operator O to operate medical equipment attached to the robot arms 21. Specifically, the remote control apparatus 10 is configured to transmit action mode instructions which are inputted by the operator O and are to be executed by the surgical instruments 40 and endoscope 50, to the patient-side apparatus 20 through the controller 26. The remote control apparatus 10 is installed beside the operation table 30 so that the operator O can see the condition of the patient P very well while operating the remote control apparatus 10, for example. The remote control apparatus 10 may be configured to transmit action mode instructions wirelessly and installed in a room different from the operation room where the operation table 30 is installed, for example.

The action modes to be executed by the surgical instruments 40 include modes of actions to be taken by each surgical instrument 40 (a series of positions and postures) and actions to be executed by the function of each surgical instrument 40. When the surgical instrument 40 is a pair of grasping forceps, for example, the action modes to be executed by the surgical instrument 40 include roll and pitch positions of the wrist of the end effector 41 and actions to open and close the jaws. When the surgical instrument 40 is a high-frequency knife, the action modes to be executed by the surgical instrument 40 include vibration of the high-frequency knife, specifically, supply of current to the high-frequency knife. When the surgical instrument 40 is a snare wire, the action modes to be executed by the surgical instrument 40 include a capturing action and an action to release the captured object and include an action to supply current to a bipolar or monopolar instrument to burn off the surgery site.

The action modes to be executed by the endoscope 50 include the position and posture of the tip or the distal end of the endoscope 50 and setting of the zoom magnification, for example.

Figure 2:
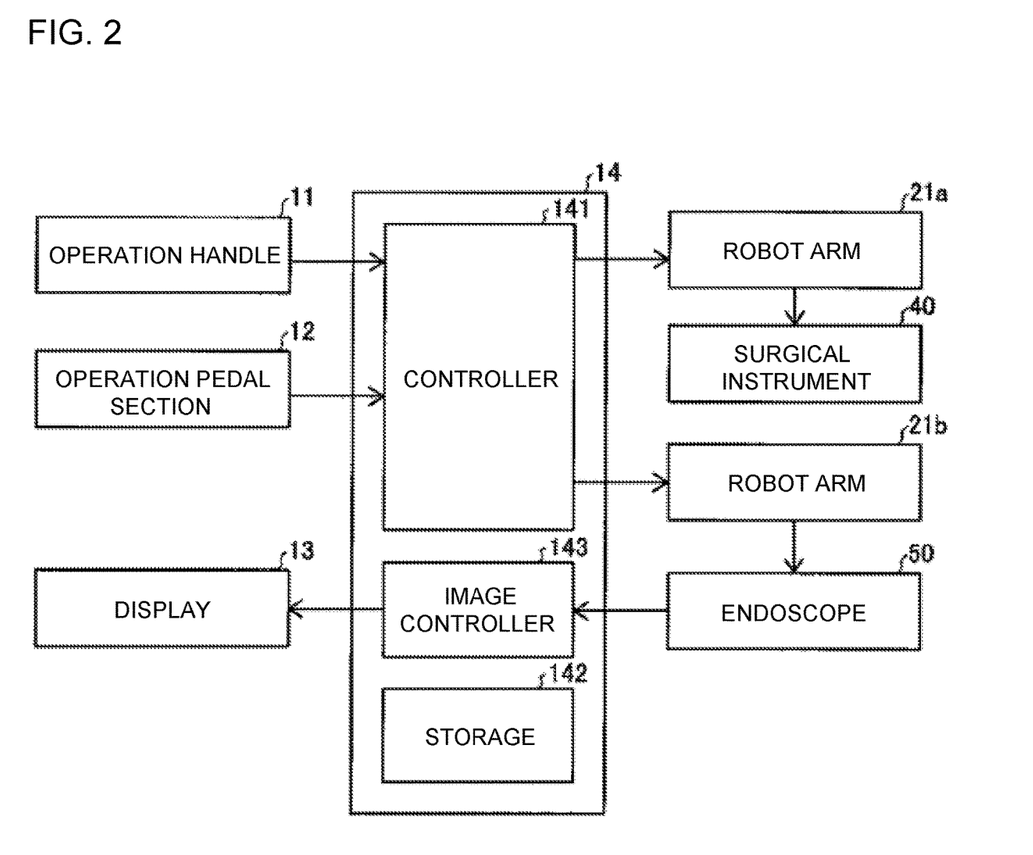
FIG. 2 is a diagram illustrating a block diagram of a control-related configuration of the robotic surgical system according to an embodiment.

As illustrated in FIGS. 1 and 2, the remote control apparatus 10 includes operation handles 11, an operation pedal section 12, a display section 13, and a control apparatus 14.

The operation handles 11 are provided in order to remotely operate medical equipment attached to the robot arms 21. Specifically, the operation handles 11 accept operations by the operator O for operating medical equipment (the surgical instruments 40 and endoscope 50). The operation handles 11 include two operation handles 11 arranged side by side in the horizontal direction. One of the two operation handles 11 is operated by the right hand of the operator O while the other operation handle 11 is operated by the left hand of the operator O.

The operation handles 11 extend from the rear side of the remote control apparatus 10 toward the front side. The operation handles 11 are configured to move in a predetermined three-dimensional operation region. Specifically, the operation handles 11 are configured so as to move up and down, right and left, and forward and rearward.

The remote control apparatus 10 and patient-side apparatus 20 constitute a master-slave system in terms of controlling movement of the robot arms 21a and robot arm 21b. The operation handles 11 constitute an operating section on the master side in the master-slave system, and the robot arms 21a and 21b holding medical equipment constitute an operating section on the slave side. When the operator O operates the operation handles 11, the movement of one of the robot arms 21a or 21b is controlled so that the tip portion or the distal end portion (the end effector 41 of the surgical instrument 40) of the robot arm 21a or the tip portion or the distal end portion (the endoscope 50) of the robot arm 21b moves following the movement of the operation handles 11.

The patient-side apparatus 20 controls the movement of the robot arms 21a in accordance with the set motion scaling ratio. When the motion scaling ratio is set to ½, for example, the end effectors 41 of the surgical instruments 40 move ½ of the movement distance of the operation handles 11. This allows precise fine surgery.

The operation pedal section 12 includes pedals to execute medical equipment-related functions. The pedals include a coagulation pedal, a cutting pedal, a camera pedal, and a clutch pedal. The pedals are operated by a foot of the operator O.

The coagulation pedal enables the surgical instrument 40 to coagulate a surgery site. Specifically, when the coagulation pedal is operated, voltage for coagulation is applied to the surgical instrument 40 to coagulate a surgery site. The cutting pedal enables the surgical instrument 40 to cut a surgery site. Specifically, the cutting pedal is operated to apply voltage for cutting to the surgical instrument 40 and cut a surgery site.

The camera pedal is used to control the position and orientation of the endoscope 50 that captures images within the body cavity. Specifically, the camera pedal enables operation of the endoscope 50 by the operation handles 11. The position and orientation of the endoscope 50 are controllable by the operation handles 11 while the camera pedal is being pressed. The endoscope 50 is controlled by using both of the right and left operation handles 11, for example. Specifically, when the operator O rotates the right and left operation handles 11 about the middle point between the right and left operation handles 11, the endoscope 50 is rotated. When the operator O presses the right and left operation handles 11 together, the endoscope 50 goes forward into the body cavity. When the operator O pulls the right and left operation handles 11 together, the endoscope 50 goes back. When the operator O moves the right and left operation handles 11 together up, down, right, or left, the endoscope 50 moves up, down, right, or left, respectively.

The clutch pedal is used to temporarily disconnect operation-related connection between the operation handles 11 and the robot arms 21 to stop movement of the surgical instruments 40. Specifically, when the clutch pedal is being operated, the robot arms 21 of the patient-side apparatus 20 do not work even if the operation handles 11 are operated. For example, when the operation handles 11 are operated and moved to the edge of the range of movement, the operator O operates the clutch pedal to temporarily disconnect the operation-related connection and then returns the operation handles 11 to the center of the range of movement. When the operator O stops operating the clutch pedal, the operation handles 11 are again connected to the robot arms 21. The operator O restarts the operation for the operation handles 11 around the center thereof.

The display section 13 is configured to display images captured by the endoscope 50. The display section 13 includes a scope type display section or a non-scope type display section. The scope type display section is a display section that the operator O looks into. The non-scope type display section is a display section like an open-type display section that includes a flat screen and the operator O is able to see without looking into, such as normal displays for personal computers.

When the scope type display section is attached, the scope type display section displays 3D images captured by the endoscope 50 attached to the robot arm 21b of the patient-side apparatus 20. When the non-scope type display section is attached, the non-scope type display section also displays 3D images captured by the endoscope 50 provided for the patient-side apparatus 20. The non-scope type display section may display 2D images captured by the endoscope 50 provided for the patient-side apparatus 20.

As illustrated in FIG. 2, the control apparatus 14 includes a controller 141, a storage 142, and an image controller 143, for example. The controller 141 includes a calculator such as a CPU. The storage 142 includes a memory, such as a ROM and a RAM. The control apparatus 14 may be formed of a single controller performing centralized control or may be composed of controllers that perform decentralized control in cooperation with each other. The controller 141 determines whether an action mode instruction inputted by the operation handles 11 is to be executed by the robot arms 21a or to be executed by the endoscope 50, depending on the state of the operation pedal section 12. When determining that the action mode instruction inputted by the operation handles 11 is to be executed by any one of the surgical instruments 40, the controller 141 transmits the action mode instruction to the corresponding robot arm 21a. The robot arm 21a is thereby driven for controlling movement of the surgical instrument 40 attached to the robot arm 21a.

When determining that the action mode instruction inputted by the operation handles 11 is to be executed by the endoscope 50, the controller 141 transmits the action mode instruction to the robot arm 21b. The robot arm 21b is thereby driven for control of movement of the endoscope 50 attached to the robot arm 21b.

The storage 142 stores control programs corresponding to the types of the surgical instrument 40, for example. The controller 141 reads the stored control programs according to the types of the attached surgical instruments 40. The action mode instructions from the operation handles 11 and/or the operation pedal section 12 of the remote control apparatus 10 thereby cause the respective surgical instruments 40 to perform proper movements.

The image controller 143 transmits images acquired by the endoscope 50 to the display section 13. The image controller 143 performs processing and alternations for the images when needed.

(Configurations of Adaptor and Surgical Instrument)

Figure 3:
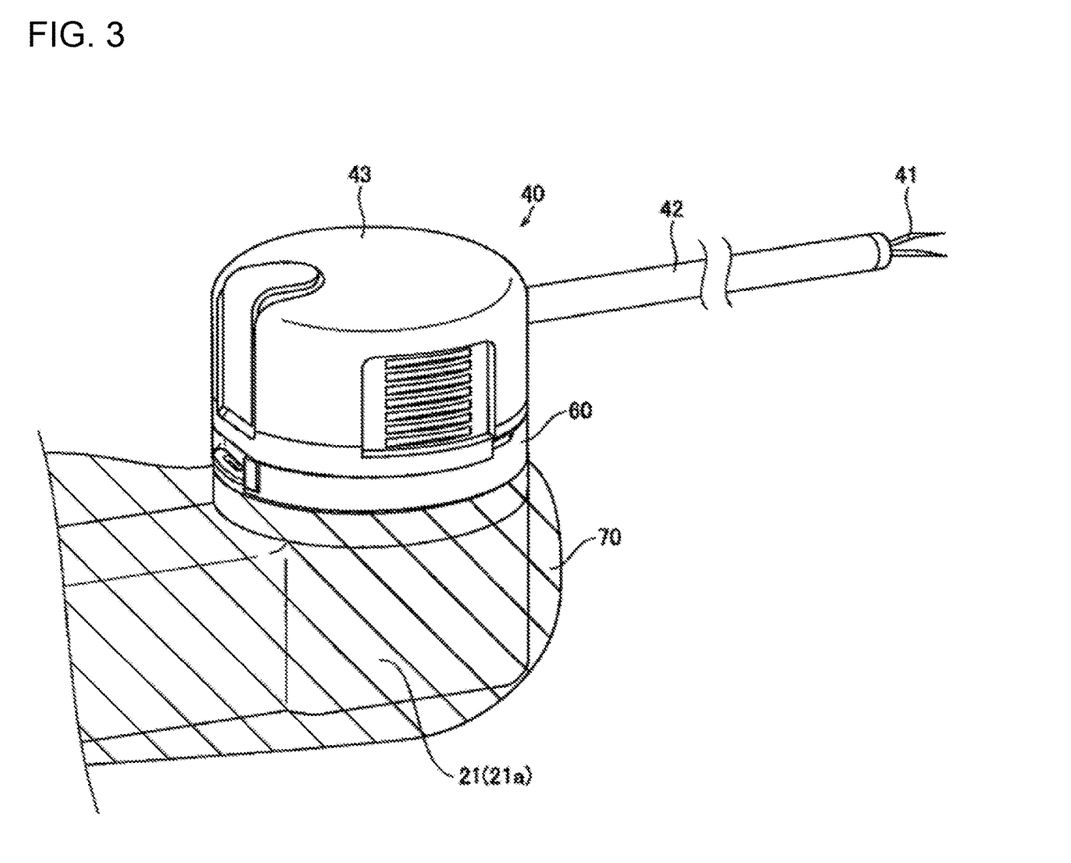
FIG. 3 is a diagram illustrating a perspective view of a state of an embodiment where a surgical instrument is attached to a robot arm through an adaptor.

With reference to FIG. 3, the configurations of an adaptor 60 and the surgical instrument 40 according to an embodiment are described.

As illustrated in FIG. 3, the robot arm 21 is used in a clean area and is covered with a drape 70. In operation rooms, clean technique is used in order to prevent surgical incision sites and medical equipment from being contaminated by pathogen, foreign matters, or the like. The clean technique defines a clean area and a contaminated area, which is other than the clean area. The surgery sites are located in the clean area. Members of the surgical team, including the operator O, make sure that only sterile objects are placed in the clean area during surgery and perform sterilization for an object which is to be moved to the clean area from the contaminated area. Similarly, when the members of the surgical team including the operator O place their hands in the contaminated area, the members sterilize their hands before directly touching objects located in the clean area. Instruments used in the clean area are sterilized or are covered with sterile drapes 70.

The drape 70 is arranged between the robot arm 21 and the surgical instrument 40. Specifically, the drape 70 is arranged between the adaptor 60 and the robot arm 21. The adaptor 60 is attached to the robot arm 21 while putting the drape 70 between the adaptor 60 and the robot arm 21. Specifically, the adaptor 60 is a drape adaptor that puts the drape 70 between the adaptor 60 and the robot arm 21. The surgical instrument 40 is attached to the adaptor 60 that is attached to the robot arm 21a with the drape 70 interposed therebetween. The robot arm 21 transmits driving force to the surgical instrument 40 through the adaptor 60 to drive the end effector 41 of the surgical instrument 40.

(Configurations of Adaptor, Endoscope Adaptor, and Endoscope)

With reference to FIGS. 4 to 9, the configurations of the adaptor 60, an endoscope adaptor 80, and the endoscope 50 according to an embodiment are described.

Figure 4:
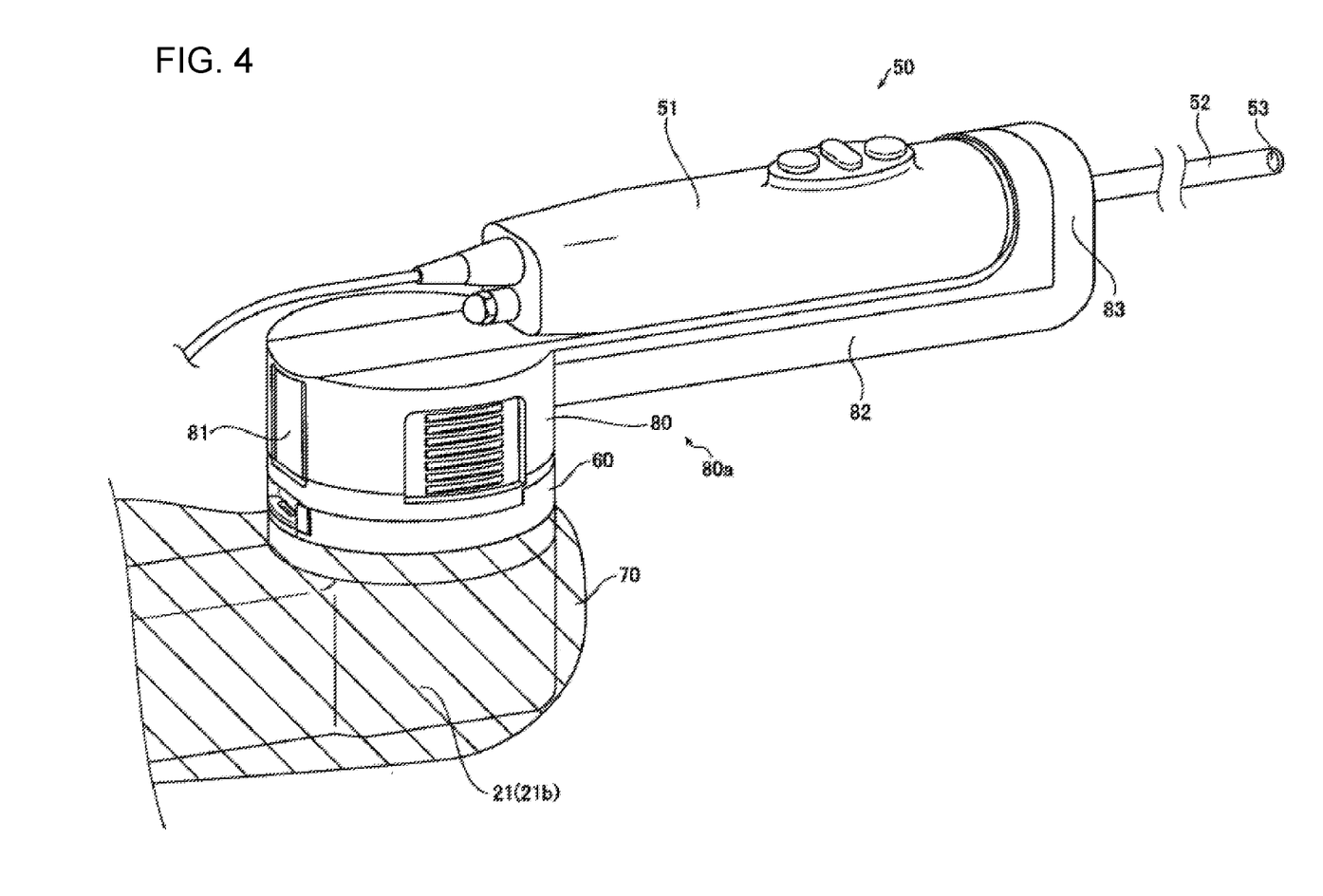
FIG. 4 is a diagram illustrating a perspective view of a state of an embodiment where an endoscope is attached to the robot arm through the adaptor.

As illustrated in FIG. 4, the endoscope 50 is rotatably held by the endoscope adaptor 80. The endoscope 50 includes a body section 51, an elongated insertion section 52, and an image capturing section 53. The endoscope 50 is held by the endoscope adaptor 80 rotatably about a rotation axis in a direction (the Y direction) in which the insertion section 52 extends (the insertion section 52—extending direction). The rotation axis about which the endoscope 50 rotates substantially coincides with the center line of the insertion section 52. The body section 51 is formed in an elongated shape extending in the Y direction. In the body section 51, one end is connected to the insertion section 52, and the other end is connected to a cable. The endoscope 50 may be a general-purpose endoscope instead of a dedicated endoscope for attachment to the robot arm 21.

The insertion section 52 is a section inserted into the body of the patient P. For example, the insertion section 52 is hard and less deformable. Specifically, the endoscope 50 is a rigid endoscope. The insertion section 52 is inserted into the body of the patient P through a trocar placed on the body surface of the patient P. The image capturing section 53 is provided at the tip or the distal end of the insertion section 52 (an end section on the opposite side of the body section 51). The image capturing section 53 can be put in the body of the patient P and can capture an image of the surgery site.

The image capturing section 53 can capture an image with one viewpoint or with plural viewpoints. Specifically, the image capturing section 53 captures an image of a target from one position or from plural positions. The image capturing section 53 includes a light. The light is turned on in the image capturing and irradiates the image capturing target with light.

The endoscope 50 being attached to the endoscope adaptor 80 is connected to the robot arm 21 (21b) of the robotic surgical system 100 through the adaptor 60 (a drape adaptor). That is, the drape 70 is arranged between the robot arm 21b and the endoscope 50. Specifically, the drape 70 is arranged between the adaptor 60 and the robot arm 21b. The adaptor 60 is attached to the robot arm 21b while putting the drape 70 between the adaptor 60 and the robot arm 21b. Specifically, the adaptor 60 is a drape adaptor that puts the drape 70 between the adaptor 60 and the robot arm 21b. The robot arm 21b transmits driving force to the endoscope adaptor 80 through the adaptor 60 to rotate the endoscope 50.

Figure 5:
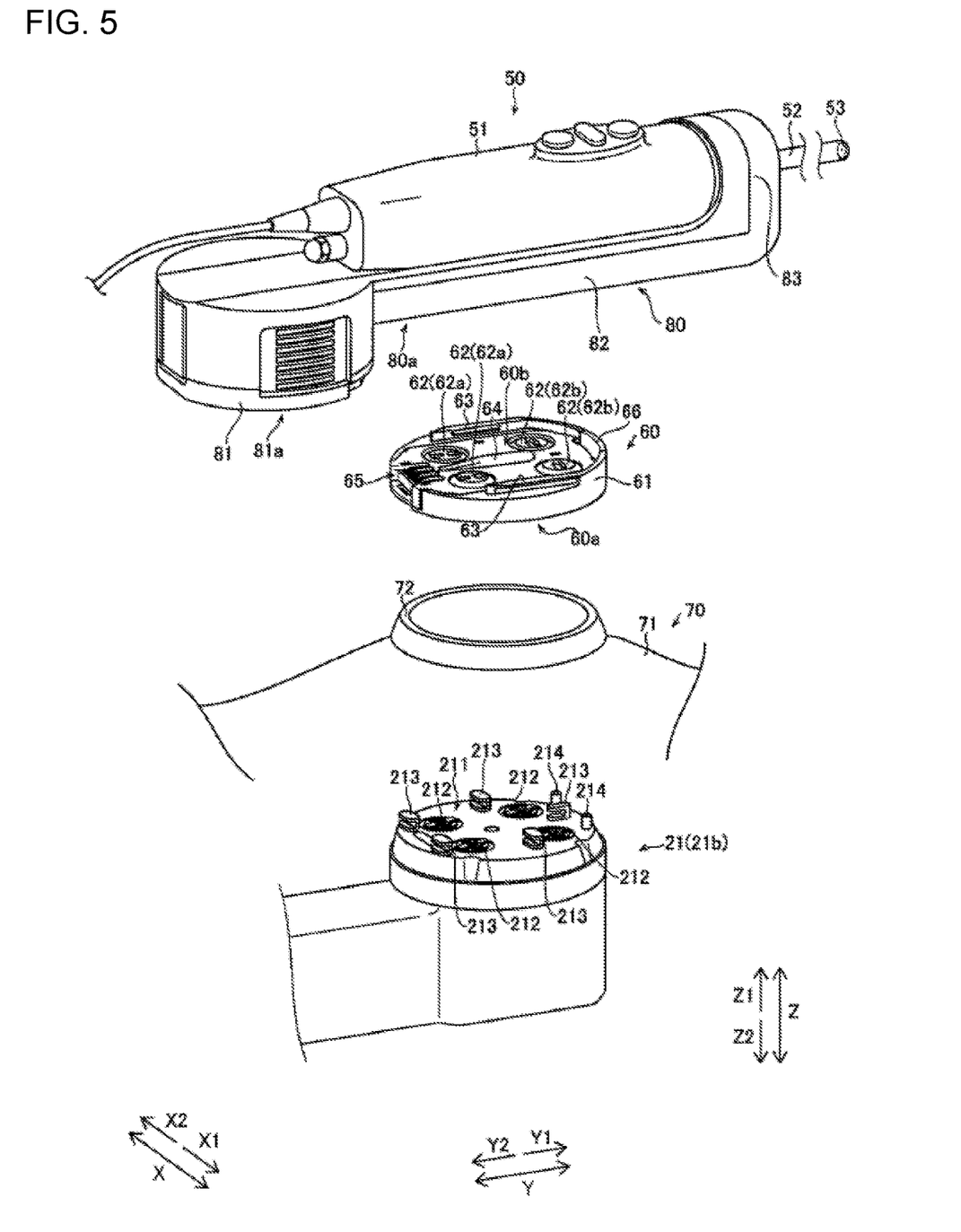
FIG. 5 is a diagram illustrating a perspective view of a state of an embodiment where the adaptor and an endoscope adaptor are detached from the robot arm.
Figure 6:
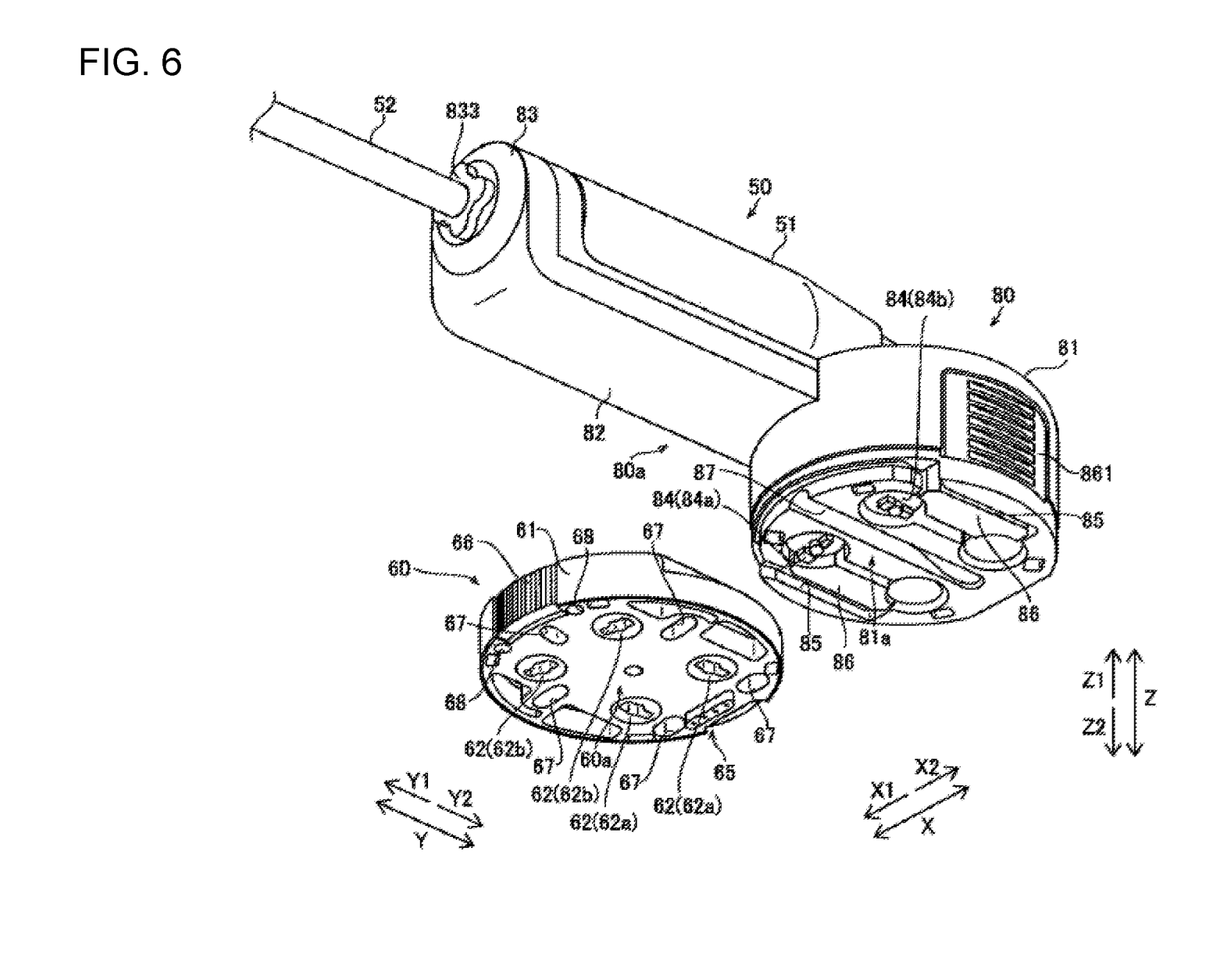
FIG. 6 is a diagram illustrating a perspective view of the endoscope adaptor and the adaptor according to an embodiment as seen from below.

As illustrated in FIG. 5, the adaptor 60 includes a base body 61, rotation drive transmission members 62, guide rails 63, a precedence guide rail 64, an electrode array 65, and an arm engagement section 66. As illustrated in FIG. 6, the adaptor 60 includes arm engagement holes 67 and positioning holes 68. As illustrated in FIG. 5, the rotation drive transmission members 62 include first rotation drive transmission members 62a arranged in the Y2 side and second rotation drive transmission members 62b arranged in the Y1 side. In the adaptor 60, a first surface 60a is arranged in the Z2 side and attached to the robot arm 21b. The adaptor 60 includes a second surface 60b arranged in the Z1 side to which the endoscope adaptor 80 is attached.

The endoscope adaptor 80 is detachably connected to the robot arm 21b of the robotic surgical system 100 through the adaptor 60. As illustrated in FIG. 5, the endoscope adaptor 80 includes a base section 80a including an attachment section 81 and an extension section 82 and a holding section 83. In the endoscope adaptor 80, an attachment surface 81a arranged in the Z2 side of the attachment section 81 is attached to the adaptor 60. As illustrated in FIG. 6, the endoscope adaptor 80 includes driven members 84, two guide grooves 85, two movable members 86, and a precedence guide groove 87. The driven members 84 include a first driven member 84a arranged in the X1 side and a second driven member 84b arranged in the X2 side.

As illustrated in FIG. 5, the drape 70 includes a body section 71 and an attachment section 72. The body section 71 is made in a film form. The attachment section 72 is made by resin molding. The attachment section 72 includes a through-opening in a section where the robot arm 21b is engaged with the adaptor 60. The through-opening may be provided corresponding to the engagement section. Through-openings may be provided corresponding to plural engagement sections.

The adaptor 60 is attached to an adaptor attachment surface 211 of the robot arm 21. The robot arm 21 includes rotation drive sections 212, engagement sections 213, and bosses 214.

As illustrated in FIG. 5, the adaptor 60 is provided to detachably connect the endoscope adaptor 80 to the robot arm 21b of the robotic surgical system 100. Specifically, the adaptor 60 can be commonly used in both the case of attaching the surgical instrument 40 to the robot arm 21 and the case of attaching the endoscope adaptor 80 to the robot arm 21. As illustrated in FIGS. 5 and 6, the base body 61 includes the first surface 60a to be attached to the robot arm 21b and the second surface 60b to which the attachment surface 81a of the endoscope adaptor 80 is mounted.

The rotation drive transmission members 62 are rotatably provided in the base body 61. Specifically, the rotation drive transmission members 62 are provided rotatably about rotation axes extending in the Z direction. The rotation drive transmission members 62 transmit driving force of the rotation drive sections 212 of the robot arm 21b to the driven members 84 of the endoscope adaptor 80.

As illustrated in FIG. 5, the guide rails 63 are provided on the second surface 60b. The guide rails 63 are provided to extend along the Y direction. The two guide rails 63 are provided to be opposed to each other in the X direction. The two guide rails 63 are provided substantially parallel to each other. The guide rails 63 are provided correspondingly to the guide grooves 85 that are provided substantially parallel to each other on the attachment surface 81a of the endoscope adaptor 80. The guide rails 63 of the second surface 60b are configured to make sliding in the Y direction between the corresponding guide rails 63 of the second surface 60b and guide grooves 85 of the attachment surface 81a and guide the endoscope adaptor 80 such that the rotation drive transmission members 62 correspond to the driven members 84 provided on the attachment surface 81a.

The two guide rails 63 of the second surface 60b are configured to guide the two guide grooves 85 of the endoscope adaptor 80 in a direction (the Y direction) crossing a direction (the Z direction) of the rotation axes of the rotation drive transmission members 62. Specifically, a direction in which the endoscope adaptor 80 is slid and inserted into the adaptor 60 is substantially parallel to the direction in which the insertion section 52 of the endoscope 50 extends (the insertion section 52—extending direction).

The precedence guide rail 64 is provided on the second surface 60b. The precedence guide rail 64 is provided to extend along the Y direction. The precedence guide rail 64 is provided between the two guide rails 63. The precedence guide rail 64 is formed to extend substantially parallel to the two guide rails 63. The precedence guide rail 64 is provided in the substantial center in the X direction of the second surface 60b. The precedence guide rail 64 is provided correspondingly to the precedence guide groove 87 provided on the attachment surface 81a. Specifically, the precedence guide rail 64 guides the endoscope adaptor 80 before the two guide rails 63 guide the endoscope adaptor 80.

The electrode array 65 is connected to the robot arm 21. The electrode array 65 is provided for connecting an electrode array of the surgical instrument 40 with the robot arm 21 when the surgical instrument 40 is connected to the adaptor 60.

As illustrated in FIGS. 5 and 6, the arm engagement section 66 is engaged with the engagement sections 213 of the robot arm 21. Specifically, the arm engagement section 66 is engaged with the engagement sections 213 that are inserted in the arm engagement holes 67 provided in the first surface 60a. The arm engagement section 66 can be moved in the Y direction. The arm engagement section 66 is biased in the Y1 direction by a bias member. The engagement of the arm engagement section 66 with the engagement sections 213 is made by moving the arm engagement section 66 in the Y1 direction. On the other hand, the engagement of the arm engagement section 66 with the engagement sections 213 is released by moving the arm engagement section 66 in the Y2 direction.

Plural arm engagement holes 67 are provided. Specifically, the adaptor 60 is fixed to the robot arm 21 by engagement of plural sections. For example, five arm engagement holes 67 are provided. The arm engagement holes 67 are provided at equal intervals along a circumferential direction of the first surface 60a.

The positioning holes 68 are provided in the first surface 60a. The bosses 214 of the robot arm 21 are fitted to the positioning holes 68. Plural positioning holes 68 are provided. The positioning holes 68 are provided near an end section in the Y1 side of the first surface 60a.

In this embodiment, as illustrated in FIG. 6, the base section 80a of the endoscope adaptor 80 is provided to be detachably connected to the adaptor 60. The base section 80a includes the attachment section 81 and the extension section 82. The attachment section 81 is attached to the adaptor 60. The extension section 82 extends from the attachment section 81 in the insertion section 52—extending direction (the Y direction). The endoscope adaptor 80 includes the holding section 83 that holds the endoscope 50 rotatably about the rotation axis in the insertion section 52—extending direction (the Y direction). The base section 80a includes the rotatably provided driven members 84 that are rotated and driven by the rotation drive sections 212 of the robot arm 21b through the adaptor 60. A transmission mechanism 88 transmits the rotation of the driven members 84 to the holding section 83 holding the endoscope 50.

While the drape 70 is put between the robot arm 21b and the adaptor 60, the rotation drive from the rotation drive sections 212 of the robot arm 21b can be transmitted to the holding section 83 holding the endoscope 50 through the adaptor 60 and the endoscope 50 can be rotated about the rotation axis in the insertion section 52—extending direction (the Y direction). In other words, it is possible to rotatably held the endoscope 50 while covering the robot arm 21b holding the endoscope 50 with the drape 70. Since the movement of the endoscope 50 other than rotation can be made by movement of the robot arm 21b, an amount of freedom of the movement of the endoscope 50 can be improved. Since an existing endoscope can be attached to the endoscope adaptor 80 instead of a dedicated endoscope for attachment to the robot arm 21b, the general-purpose versatility can be improved.

As illustrated in FIG. 6, the driven members 84 of the endoscope adaptor 80 are rotated and driven to rotate the endoscope 50. For example, two driven members 84 are provided. The robot arm 21 includes four rotation drive sections 212. The adaptor 60 includes four rotation drive transmission members 62 engaged with the rotation drive sections 212. The surgical instrument 40 may also be attached to the robot arm 21 through the adaptor 60. In this case, the surgical instrument 40 is driven by the four rotation drive sections 212. For example, the shaft 42 of the surgical instrument 40 is rotated by the rotation of one rotation drive section 212, and the end effector 41 is driven by the rotation of the other three rotation drive sections 212.

Specifically, the driven members 84 are rotated by the rotation of the rotation drive sections 212 of the robot arm 21b that is transmitted by the rotation drive transmission members 62 of the adaptor 60. The rotation drive transmission members 62 can transmit the rotation drive of the rotation drive sections 212 of the robot arm 21b easily to the driven members 84 of the endoscope adaptor 80.

Figure 7:
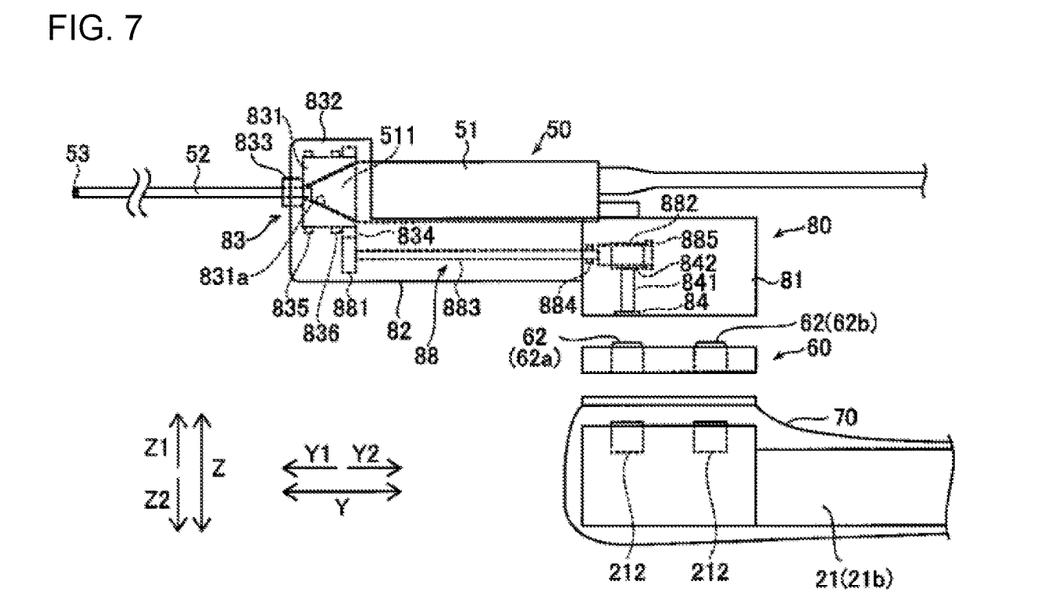
FIG. 7 is a diagram illustrating a side view of the endoscope adaptor, the adaptor, and the robot arm according to an embodiment.

As illustrated in FIG. 7, a helical gear 842 is connected to each driven member 84 through a shaft 841. The helical gear 842 rotates about a rotation axis in the Z direction in accordance with the rotation of the driven member 84.

As illustrated in FIG. 6, the driven members 84 are arranged in the slide insertion direction upstream side (the Y1 side). The driven members 84 are engaged with the second rotation drive transmission members 62b of the adaptor 60. The driven members 84 have a shape that is not engaged with the first rotation drive transmission members 62a. This makes it possible to prevent the driven members 84 from being engaged and stuck with the first rotation drive transmission members 62a during the sliding of the endoscope adaptor 80 with respect to the adaptor 60.

The two guide grooves 85 are provided on the attachment surface 81a of the attachment section 81. The two guide grooves 85 are provided to receive the two guide rails 63 provided on the adaptor 60 by allowing them to slide therein. The guide grooves 85 are provided to extend along the Y direction. The two guide grooves 85 are provided to be opposed to each other in the X direction. The two guide grooves 85 are provided substantially parallel to each other. The two guide rails 63 of the adaptor 60 are respectively inserted into the two guide grooves 85, and the two guide grooves 85 thus guide attachment of the endoscope adaptor 80 to the adaptor 60.

The width of each guide groove 85 is varied according to movement in the X direction of the corresponding movable member 86. Specifically, when the movable member 86 is moved inward, the width of the guide groove 85 is increased. When the movable member 86 is moved outward, the width of the guide groove 85 is decreased. The movable member 86 is biased to a direction (the outward direction) in which the width of the guide groove 85 is decreased. Specifically, the movable member 86 is biased by a spring. When a worker presses the corresponding button 861, the movable member 86 is moved in a direction (the inward direction) in which the width of the guide groove 85 is increased.

The precedence guide groove 87 is provided to extend along the Y direction. The precedence guide groove 87 is provided between the two guide grooves 85. The precedence guide groove 87 is formed to extend substantially parallel to the two guide grooves 85. The precedence guide groove 87 is provided in the substantial center in the X direction of the attachment surface 81a.

As illustrated in FIG. 7, the holding section 83 includes a first holding member 831 and a second holding member 832. The holding section 83 includes a fix member 833. A first gear 834 is provided on an outer circumference of the first holding member 831. The holding section 83 is provided to continue to the tip or the distal end of the extension section 82 extending in the Y direction. Specifically, the holding section 83 is provided on the tip side or the distal end side of the extension section 82. Since the extension section 82 can separate the position of the adaptor 60 and the position of the holding section 83 from each other, it is possible to prevent the body section 51 of the endoscope 50 from sticking out to the robot arm 21b side (the opposite side of the holding section 83) of the adaptor 60.

The first holding member 831 holds the endoscope 50. The second holding member 832 is included in the base section 80a and rotatably holds the first holding member 831. Specifically, the first holding member 831 is rotatably held by the second holding member 832 through bearings 835 and 836. That is, the first holding member 831 is connected to inner circumferential sections of the bearings 835 and 836, and the second holding member 832 is connected to outer circumferential sections of the bearings 835 and 836. Since the first holding member 831 holding the endoscope 50 can be rotatably held by the second holding member 832 stably, it is possible to suppress displacement of the position of the image capturing section 53 at the tip of the endoscope 50 with respect to the robot arm 21b.

A through-hole is formed to penetrate in the Y direction through the first holding member 831. The diameter of an opening in the Y1 side of the first holding member 831 is formed greater than the diameter of the insertion section 52 of the endoscope 50 but smaller than the diameter of the body section 51 of the endoscope 50. The diameter of an opening in the Y2 side of the first holding member 831 is formed greater than the diameter of the body section 51 of the endoscope 50.

The first holding member 831 includes an inner wall 831a along (corresponding to) the shape of a section in the insertion section 52 side (the Y1 side) of the body section 51 of the endoscope 50. Specifically, a tip section 511 or a distal end portion 511 of the body section 51 of the endoscope 50 is provided in the Y1 side of the body section 51. The inner wall 831a of the first holding member 831 is formed in a shape along (corresponding to) the tip section 511 of the body section 51. The outer circumference of the body section 51 of the endoscope 50 can be closely attached to the inner wall 831a of the first holding member 831. Consequently, the first holding member 831 can hold the endoscope 50 stably.

Specifically, the tip section 511 is formed in a tapered shape having a circular cross-section. In other words, the tip section 511 is formed in a conical shape. The first holding member 831 includes the conical inner wall 831a along (corresponding to) the conical shape of the tip section 511 in the insertion section 52 side of the body section 51 of the endoscope 50. Even when the central angle of the cone of the body section 51 of the endoscope 50 is little different from the central angle of the cone of the inner wall 831a of the first holding member 831, sections having the equal diameters can come into contact with each other on the corresponding circumferential lines. Consequently, excessive pursuit of the dimension accuracy of the inner wall 831a of the first holding member 831 is unnecessary for the first holding member 831 to hold the endoscope 50 stably. Since the endoscope 50 may also be an endoscope including a cone with the central angle different from the central angle of the cone of the inner wall 831a of the first holding member 831, it is easier to apply an existing endoscope.

Figure 8:
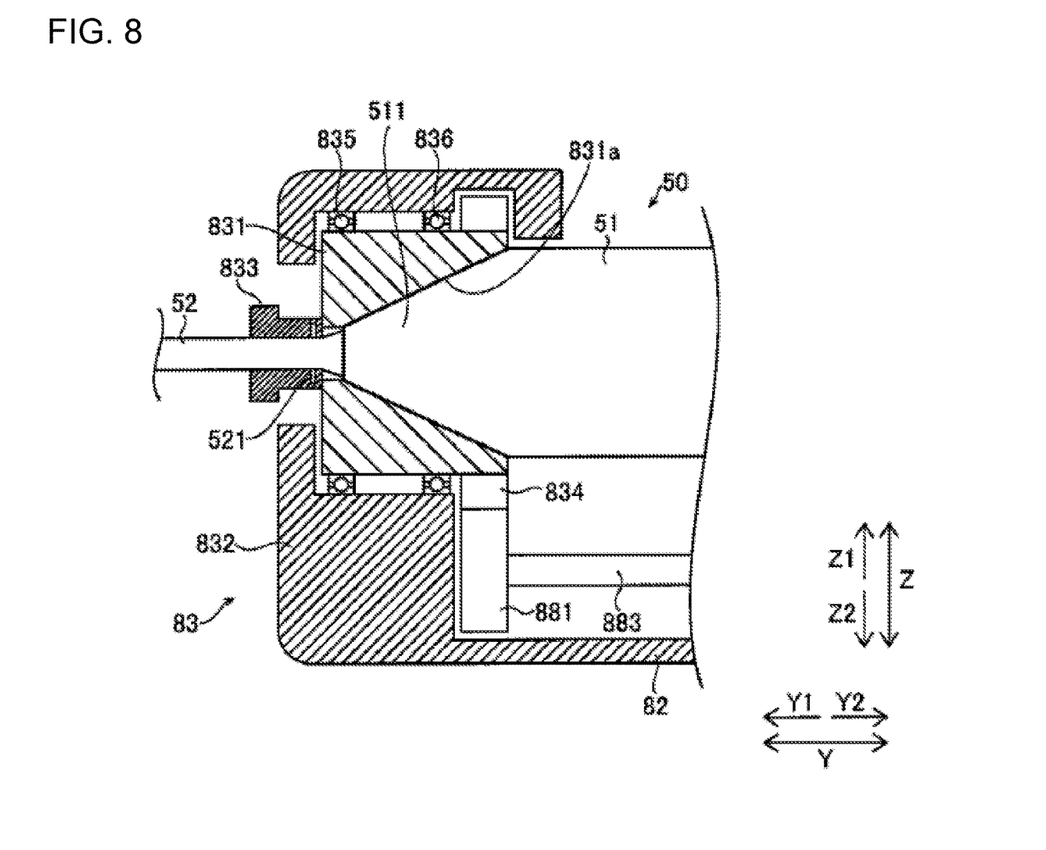
FIG. 8 is a diagram illustrating an explanatory view of holding of the endoscope by the endoscope adaptor according to an embodiment.

As illustrated in FIG. 8, the fix member 833 is put in contact with a tip section or distal end of the first holding member 831 and engaged with an engagement section 521 of the insertion section 52 of the endoscope 50 such that the body section 51 is pressed onto the inner wall 831a of the first holding member 831. Specifically, the engagement section 521 in the form of a male screw is provided on the insertion section 52 of the endoscope 50. The fix member 833 is in the form of a female screw. With the fix member 833 engaged with the engagement section 521 and rotated to be tightened, a distance is reduced between the fix member 833 and the body section 51, which are sandwiching the first holding member 831. The body section 51 of the endoscope 50 can be more closely attached to the inner wall 831a of the first holding member 831. Consequently, the first holding member 831 can hold the endoscope 50 more stably.

Specifically, when attaching the endoscope 50 to the first holding member 831, the insertion section 52 of the endoscope 50 is inserted into the first holding member 831 from the Y2 side. The fix member 833 is engaged with the engagement section 521 and tightened while the inner wall 831a of the first holding member 831 is put in contact with the tip section 511 of the endoscope 50, and thus the endoscope 50 is fixed with respect to the first holding member 831. When detaching the endoscope 50 from the first holding member 831, the fix member 833 is loosened to release the engagement with the engagement section 521 first, and then the insertion section 52 of the endoscope 50 is moved to the Y2 side with respect to the first holding member 831 and pulled out.

The body section 51 of the endoscope 50 is supported in the endoscope adaptor 80, while being in contact with only the first holding member 831 and the fix member 833. Specifically, when the endoscope 50 is attached to the first holding member 831, a section other than the attachment section of the body section 51 of the endoscope 50 is distant (suspended) from the endoscope adaptor 80.

As illustrated in FIG. 7, the transmission mechanism 88 includes a second gear 881, a cylindrical worm gear 882, a shaft 883, and bearings 884 and 885. The second gear 881 is provided coaxially with the cylindrical worm gear 882. Specifically, the second gear 881 and the cylindrical worm gear 882 are respectively provided on one end and the other end of the linearly extending shaft 883. The second gear 881 is provided on the end section in the Y1 side of the shaft 883. The cylindrical worm gear 882 is provided on the end section in the Y2 side of the shaft 883. The second gear 881 meshes with the first gear 834. The first holding member 831 is rotated by the rotation of the second gear 881. The number of teeth of the second gear 881 is smaller than the number of teeth of the first gear 834. Consequently, the transmission mechanism 88 reduces the rotational speed of the driven members 84 and transmits the reduced rotational speed to the first gear 834.

The cylindrical worm gear 882 meshes with the helical gears 842 of the driven members 84. The helical gears 842 and the cylindrical worm gear 882 can change the rotation axis directions of the rotation from the rotation drive sections 212 of the robot arm 21b to transmit the rotation, and thus the second gear 881 can rotate the first holding member 831 holding the endoscope 50. In addition, it is unnecessary to provide a gear in the endoscope 50 itself by providing in the holding section 83 of the endoscope adaptor 80 the first holding member 831 including the first gear 834 formed on the outer circumference. Thus, a general-purpose existing endoscope may be used.

For example, at least either of the helical gears 842 and the cylindrical worm gear 882 is a resin gear. Comparing with a case of using a metal gear, the resin gear can suppress generation of noises and vibrations due to the mesh of the gears. The elastic deformation of the resin gear can reduce backlash. Both the helical gears 842 and cylindrical worm gear 882 may be made of metal.

Figure 9:
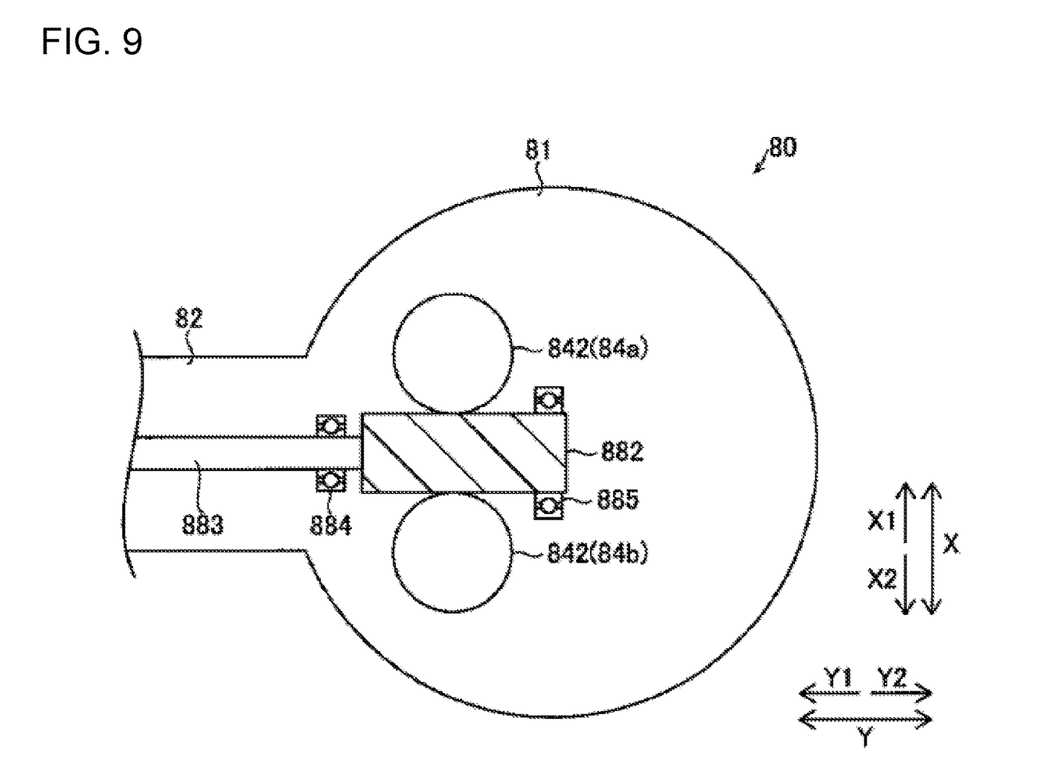
FIG. 9 is a diagram illustrating an explanatory view of driving of a driven member of the endoscope adaptor according to an embodiment.

As illustrated in FIG. 9, one of the first driven member 84a and the second driven member 84b may be driven to rotate forward (in a positive rotational direction) and the other may be driven to rotate backward (in a negative rotational direction) to transmit the drive. Each of the first driven member 84a and the second driven member 84b can be rotated and driven in only one direction. Consequently, it is possible to suppress the generation of backlash.

One of the first driven member 84a and the second driven member 84b may be driven to rotate forward and backward to transmit the drive and the other may be driven by the drive from the one. Only one driven member 84 out of the first driven member 84a and the second driven member 84b needs to be rotated and driven. Consequently, it is possible to simplify the apparatus configuration.

The bearing 884 rotatably supports a section of the shaft 883 near the cylindrical worm gear 882. The bearing 885 rotatably supports a section of the cylindrical worm gear 882 near the end section in the Y2 side. Specifically, the bearings 884 and 885 rotatably support the cylindrical worm gear 882 by sandwiching the position in which the helical gears 842 mesh with the cylindrical worm gear 882.

A plurality of the robot arms 21 are provided to respectively attach the surgical instruments 40 and the endoscope 50 thereto. The endoscope adaptor 80 (the endoscope 50) can be mounted to any of the robot arms 21. Since the endoscope 50 can be mounted to any of the robot arms 21, an amount of freedom of the attachment of the endoscope 50 can be improved. Common adaptors 60 can be used to attach the surgical instruments 40 and the endoscope 50 to the robot arms 21.

(Attachment of Endoscope to Robot Arm)

With reference to FIG. 5, attachment of the endoscope 50 (the endoscope adaptor 80) to the robot arm 21b according to an embodiment is described.

As illustrated in FIG. 5, the adaptor 60 is attached to the robot arm 21b while covering the robot arm 21b with the drape 70. The adaptor 60 is attached to the robot arm 21b while moving the adaptor 60 in the Z direction with respect to the robot arm 21b. The endoscope adaptor 80 holding the endoscope 50 is attached to the adaptor 60 that is attached to the robot arm 21b. The endoscope adaptor 80 is attached to the adaptor 60 while moving the endoscope adaptor 80 in the Y direction along the precedence guide rail 64 and the two guide rails 63. In this way, the endoscope adaptor 80 (the endoscope 50) is attached to the robot arm 21b through the adaptor 60.

When detaching the endoscope adaptor 80 from the robot arm 21b, the endoscope adaptor 80 is slid and moved in the Y2 direction while pressing the buttons 861 of the movable members 86 of the endoscope adaptor 80 to detach the endoscope adaptor 80 from the adaptor 60.

(Modifications)

It should be understood that the embodiments disclosed herein are illustrated by way of example in every respect and do not limit the invention. The scope of the present invention is indicated by claims, not by explanation of the embodiments, and includes equivalents to claims and all alterations (modifications) within the same.

For example, the endoscope adaptor is slid and moved in the insertion section-extending direction along the second surface of the adaptor (the drape adaptor) in the example of attachment and detachment illustrated in an above-described embodiment, but the invention is not limited thereto. In an embodiment or a modification, the endoscope adaptor may be attached and detached by being slid and moved in a direction crossing the insertion section-extending direction along the second surface of the drape adaptor.

The endoscope adaptor may be attached and detached without being slid and moved with respect to the drape adaptor. For example, the endoscope adaptor may be attached and detached by being moved in a direction in which the endoscope adaptor is engaged with the drape adaptor.

The holding section supports the tip in the insertion section side of the body section of the endoscope in the example illustrated in an above-described embodiment, but the invention is not limited thereto. In an embodiment or a modification, the holding section may support the insertion section of the endoscope or may support a section other than the tip in the insertion section side of the body section of the endoscope.

The adaptor (the drape adaptor) is a substantial circle in plan view in the example illustrated in an above-described embodiment, but the invention is not limited thereto. In an embodiment or a modification, the shape of the drape adaptor in plan view may not be a substantial circle. For example, the drape adaptor may be a rectangle in plan view.

Two driven members are provided in the endoscope adaptor in the example illustrated in an above-described embodiment, but the invention is not limited thereto. In an embodiment or a modification, one driven member may be provided in the endoscope adaptor, or three or more driven members may be provided in the endoscope adaptor.

Common adaptors (drape adaptors) are used in both the case of attaching the surgical instrument to the robot arm and the case of attaching the endoscope adaptor to the robot arm in the example illustrated in an above-described embodiment, but the invention is not limited thereto. Different types of drape adaptors may be used in the case of attaching the surgical instrument to the robot arm and the case of attaching the endoscope adaptor to the robot arm in an above-described embodiment.

The adaptor (the drape adaptor) and the drape are separately provided in the example illustrated in an above-described embodiment, but the invention is not limited thereto. In an embodiment or a modification, the drape adaptor and the drape may be integrally provided.

The invention claimed is:

1. An endoscope adaptor to be connected to a robot arm of a robotic surgical system through a drape adaptor, comprising:
    a base section that is to be detachably connected to the drape adaptor;

a driven member that is rotatably provided on the base section and is configured to be rotated by a rotation drive section of the robot arm through the drape adaptor;

a holding section that holds an endoscope rotatably about a rotation axis, the endoscope including an insertion section including an image capturing section provided at a distal end of the insertion section and a body section connected to the insertion section, wherein the rotation axis extends in a direction in which the insertion section extends; and a transmission mechanism configured to transmit rotation of the driven member to the holding section holding the endoscope, wherein the holding section includes: a first holding member that holds the endoscope and includes a first gear formed on an outer circumference of the first holding member; and a second holding member that rotatably holds the first holding member, and the transmission mechanism includes a second gear that meshes with the first gear, such that the transmission mechanism rotates the first holding member of the holding section by rotation of the second gear.

2. The endoscope adaptor according to claim 1, wherein the driven member includes a helical gear, and the transmission mechanism includes a cylindrical worm gear that meshes with the helical gear of the driven member and the second gear that is provided coaxially with the cylindrical worm gear and meshes with the first gear, such that the transmission mechanism rotates the first holding member of the holding section by rotation of the second gear.

3. The endoscope adaptor according to claim 2, wherein the transmission mechanism reduces rotational speed of the driven member and transmits the reduced rotational speed to the first gear.

4. The endoscope adaptor according to claim 3, wherein the number of teeth of the second gear is less than the number of teeth of the first gear.

5. The endoscope adaptor according to claim 2, wherein at least one of the helical gear and the cylindrical worm gear is a resin gear.

6. The endoscope adaptor according to claim 2, wherein the first holding member includes an inner wall along a shape of an insertion section side of the body section of the endoscope.

7. The endoscope adaptor according to claim 6, wherein the first holding member includes a conical inner wall along a conical shape of an insertion section side of the body section of the endoscope.

8. The endoscope adaptor according to claim 6, wherein the holding section further includes a fix member that is in contact with a distal end of the first holding member and engaged with an engagement section of the insertion section of the endoscope such that the body section is pressed onto the inner wall of the first holding member.

9. The endoscope adaptor according to claim 8, wherein the engagement section is in a male screw form, and the fix member is in a female screw form.

10. The endoscope adaptor according to claim 2, wherein the first holding member is rotatably held by the second holding member through bearings.

11. The endoscope adaptor according to claim 1, wherein the base section includes: an attachment section that is to be attached to the drape adaptor; and an extension section that extends from the attachment section in the direction in which the insertion section extends, and the holding section is provided on a distal end side of the extension section.

12. The endoscope adaptor according to claim 11, wherein the attachment section includes two guide grooves to receive two guide rails provided in the drape adaptor such that the two guide rails of the drape adaptor are slidable in the two guide grooves.

13. The endoscope adaptor according to claim 12, wherein the attachment section includes, between the two guide grooves, a precedence guide groove which is provided corresponding to a precedence guide rail provided between the two guide rails on the drape adaptor.

14. The endoscope adaptor according to claim 1, wherein the driven member includes a first driven member and a second driven member, and one of the first driven member and the second driven member is driven to rotate forward and the other is driven to rotate backward to transmit drive.

15. The endoscope adaptor according to claim 1, wherein the driven member includes a first driven member and a second driven member, and one of the first driven member and the second driven member is driven to rotate forward and backward to transmit drive and the other is driven by the drive from the one driven member.

16. The endoscope adaptor according to claim 1, wherein the driven member is rotated by rotation of a rotation drive transmission member that is provided in the drape adaptor and is rotated by the rotation drive section of the robot arm.

17. The endoscope adaptor according to claim 1, wherein the endoscope is a rigid endoscope.

18. The endoscope adaptor according to claim 1, wherein the driven member is provided such that a direction in which a rotation axis of the driven member extends crosses the direction in which the insertion section of the endoscope extends.

19. The endoscope adaptor according to claim 1, wherein the second holding member rotatably holds the first holding member at a position corresponding to an end portion of the body section of the endoscope on a side of the insertion section of the endoscope.

20. A robotic surgical system, comprising:

a robot arm that is covered with a drape and includes a rotation drive section;

a drape adaptor that is attached to the robot arm and includes a rotation drive transmission member engaged with the rotation drive section; and an endoscope adaptor that is attached to the drape adaptor and includes a driven member engaged with the rotation drive section, a holding section rotatably holding an endoscope, and a transmission mechanism transmitting rotation of the driven member to the holding section, wherein the holding section includes: a first holding member that holds the endoscope and includes a first gear formed on an outer circumference of the first holding member; and a second holding member that rotatably holds the first holding member, and the transmission mechanism includes a second gear that meshes with the first gear, such that the transmission mechanism rotates the first holding member of the holding section by rotation of the second gear.

21. The robotic surgical system according to claim 20, wherein
the robot arm comprises a plurality of robot arms provided to respectively attach a surgical instrument and the endoscope thereto, and
the endoscope is mountable to any of the plurality of robot arms.

22. A method of attaching an endoscope to a robot arm through a drape adaptor and an endoscope adaptor, comprising:
attaching the endoscope to a holding section of the endoscope adaptor such that the endoscope is rotatably held by the holding section of the endoscope adaptor;
attaching the drape adaptor to the robot arm such that a rotation drive section of the robot arm is engaged with a rotation drive transmission member of the drape adaptor in a state where the robot arm is covered with a drape; and
attaching the endoscope adaptor that holds the endoscope to the drape adaptor attached to the robot arm such that a driven member of the endoscope adaptor that is configured to transmit rotation to the holding section through a transmission mechanism is engaged with the rotation drive transmission member of the drape adaptor, wherein
the holding section includes: a first holding member that holds the endoscope and includes a first gear formed on an outer circumference of the first holding member; and a second holding member that rotatably holds the first holding member, and
the transmission mechanism includes a second gear that meshes with the first gear, such that the transmission mechanism rotates the first holding member of the holding section by rotation of the second gear.

* * * * *